United States Patent [19]

Hinohara et al.

[11] Patent Number: 4,696,919

[45] Date of Patent: Sep. 29, 1987

[54] METHOD OF PREVENTING AND TREATING OBESITY

[75] Inventors: Yoshikazu Hinohara, Gunma; Rokuro Kaifu; Isao Matsunaga, both of Tokyo, all of Japan

[73] Assignee: Chugai Seiyaku Kabushiki Kaisha, Tokyo, Japan

[21] Appl. No.: 660,421

[22] Filed: Oct. 10, 1984

[30] Foreign Application Priority Data

Oct. 13, 1983 [JP] Japan ............................... 58-192015

[51] Int. Cl.$^4$ ............................................. A61K 31/70
[52] U.S. Cl. ....................................... 514/62; 536/55.2
[58] Field of Search .................. 514/62; 536/18.7, 55.2

[56] References Cited

U.S. PATENT DOCUMENTS 2,907,697 10/1959 Costello et al. ...................... 514/62

OTHER PUBLICATIONS

Mega et al, "N-Acetyl-β-D-Glucosaminidase of Aspergillus Oryzae . . . ", Chem. Abstr., vol. 78, No. 15, Apr. 16, 1973, p. 195, 94359j.
Mommsen, "Chitinase and β-N-Acetylglucosaminidase from the Digestive Fluid of the Spider, Cupiennius salei", Chem. Abstr. 92:193322n, vol. 92, No. 23, Jun. 9, 1980, p. 245.
Grajeswar et al, "Synthesis and Biological Activity of Some 1-N-Substituted Acetamido-2-Deoxy-β-D--Glycopyranosylamine Derivatives and Related Analogs" Carbohydrate Research; 80 (1980) 99–115, Elsevier Scientific Publishing Co.
Ng Ying Kin et al, "The Deamination of Pyranose Amines, Part I, Equatorial Aines", J. Chem. Soc(C), 1971, pp. 1578–1583.
T. Sakata et al., Feeding and Hyperglycemia Induced by 1,5-Anhydroglucitol in the Rat (Physiol. Behav., 27: 401–405, 1981).
K. Tsutsui et al., Feeding Suppression Induced by Intra–Ventricle III Infusion of 1,5-Anhydroglucitol (Physiol. Behav. 31; 493–502, 1983).

Primary Examiner—J. R. Brown
Attorney, Agent, or Firm—Browdy and Neimark

[57] ABSTRACT

A method of diminishing appetite, in turn preventing and treating obesity, by administration of a compound of the formula

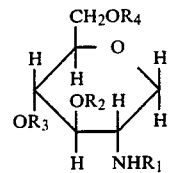

wherein $R_1$, $R_2$, $R_3$ and $R_4$ are the same or different and selected from a hydrogen atom or an acetyl group, or its pharmaceutically acceptable acid addition salt, and a pharmaceutical composition containing as an active ingredient the compound represented by the above formula.

6 Claims, 14 Drawing Figures

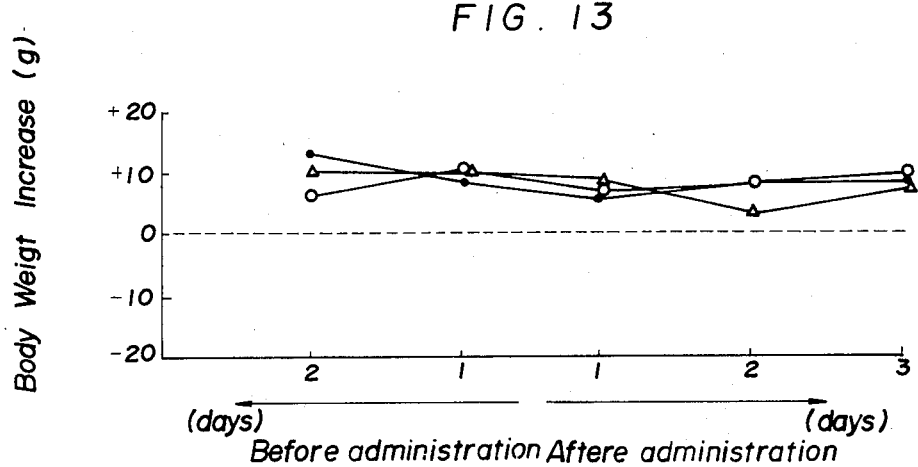
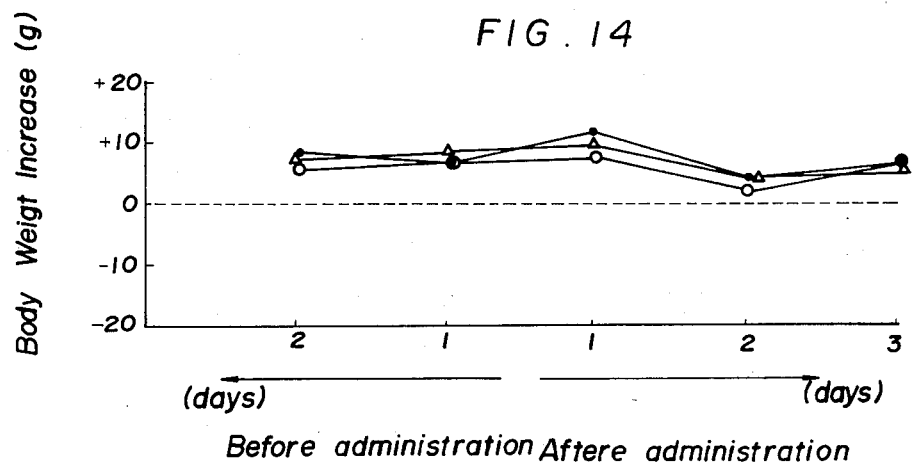

METHOD OF PREVENTING AND TREATING OBESITY

FIELD OF THE INVENTION

This invention relates to a method of diminishing appetite, in turn preventing and treating obesity, by administration of a compound of the formula

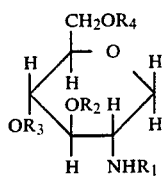

wherein $R_1$, $R_2$, $R_3$ and $R_4$ are the same or different and selected from a hydrogen atom or an acetyl group, or its pharmaceutically acceptable acid addition salt. This invention also relates to a pharmaceutical composition containing as an active ingredient the compound represented by the above formula.

BACKGROUND OF THE INVENTION

Amphetamines or an amphetamine-like anorectic agents have been used to depress excessive intake of food and water, thus preventing or treating obesity, which causes or aggravates various clinically serious diseases such as hypertension, myocardial infarction, diabetes, and renopathy. However, these compounds have adverse side effects such as dependence erethism and insomnia, caused by stimulation of the central nervous system by these compounds.

Therefore, it has long been desired to develop medicines in the clinical field for diminishing appetite free from such adverse side effects.

Recently, several important studies concerning the action of glucose sensitive neurons have been reported, and the direction of research and development concerning anorectic action has been remarkably changed. Among these studies, reports concerning deoxy-D-glucose, which has interesting strong and unique biological actions and is similar in structure to glucose have attracted attention (Sakata et al., Record of the First Study Meeting Concerning Obesity, 18-20, (1980)).

Deoxy-D-glucose is wrongly identified by glucose-sensitive neurons because of its structural similarity and is taken into cells. As a result, normal metabolism of glucose-6-phosphoric acid is terminated, the function of the glucose sensitive neurons is depressed, and in turn depression of intake of food and water is exhibited for a prolonged period. However, this compound also exhibits relatively strong side effects causing disorder in other parts of the nervous system and therefore the clinical use thereof is dangerous.

SUMMARY OF THE INVENTION

In view of this situation, the present inventors directed their research toward finding compounds which act selectively on the feeding center to decrease intake of food and water and exhibit very low side effects, thereby being useful for preventing and treating obesity, eventually finding the compounds represented by the formula (I). These compounds exhibit ataxia-like side effects lower than those induced when deoxy-D-glucose is administered and have a high ratio of effectiveness in decreasing intake of food and water as against adverse side effects, and are therefore of value for clinical use.

BRIEF EXPLANATION OF THE DRAWINGS

FIG. 1: 1-deoxyglucosamine (intraperitoneally)
FIG. 2: 1-deoxyglucosamine (orally)
FIG. 3: 1-deoxy-N-acetylglucosamine (orally)
FIG. 4: 1-deoxy-tetraacetylglucosamine (orally)
FIG. 5: D-glucose (intraperitoneally)
FIG. 6: physiological saline (intraperitoneally)
FIG. 7: no compound administered FIGS. 8-14 show a change in body weight with passage of time measured in days with respect to groups of rats administered an active compound of this invention or other material.

FIG. 8: 1-deoxyglucosamine (intraperitoneally)
FIG. 9: 1-deoxyglucosamine (orally)
FIG. 10: 1-deoxy-N-acetylglucosamine (orally)
FIG. 11: 1-deoxy-tetraacetylglucosamine (orally)
FIG. 12: D-glucose (intraperitoneally)
FIG. 13: physiological saline (intraperitoneally)
FIG. 14: no compound administered The compounds represented by the formula (I) involve, for example, 1-deoxyglucosamine, 1-deoxy-N-acetylglucosamine, 1-deoxy-tetraacetylglucosamine, etc. The preparation and physical properties of these compounds have been reported in for example, Journal of the Chemical Society (C), pp. 1578-1583, (1971), and The Journal of Organic Chemistry Vol. 27, pp. 1794-1800 (1962). However, pharmacological activities of these compounds have not yet been reported.

Figure 1:
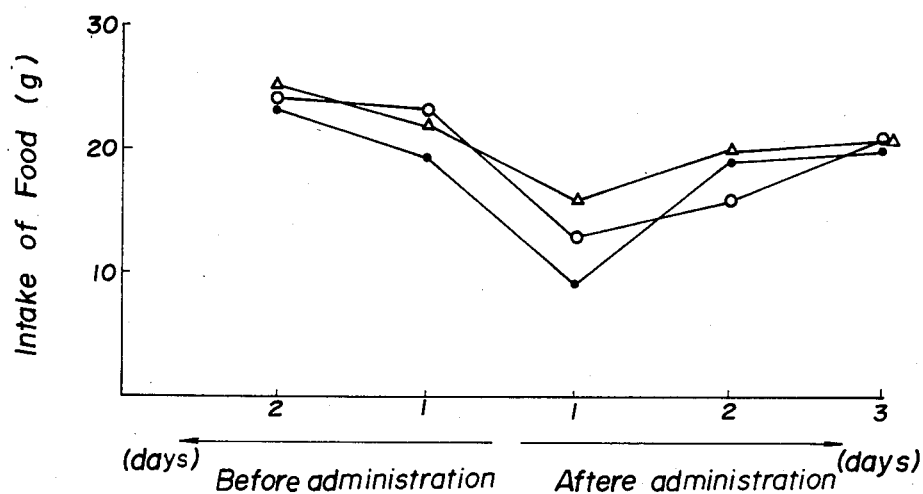
FIGS. 1-7 show a change in food intake with passage of time measured in days with respect to groups of rats administered an active compound of this invention or other material.

The anorectic compounds of this invention may be used for the purpose of treating or preventing obesity by orally or parenterally administering them in various formulations and preparation forms. Examples of preparation forms are capsules, granules, powder, tablets, syrup, suspension and injections.

The preparation may be formulated by any conventional method, using one or more known additives such as excipient, binder, disintegrator, lubricant, flavoring, preservative, stabilizer, etc.

The dose varies depending on age, weight, symptoms, etc. of the patient to be treated. However, an average adult is usually administered a compound of the formula (I) or its acid addition salt in a dose of from 10 to 1,000 mg/day, preferably from 50 to 500 mg/day, wich may be separately administered 1-3 times a day. Examples of the amount per dose are 10, 50, and 100 mg (the amount are of course not limited to these examples).

The following experiment is provided to explain the anorectic action and weight decreasing effects exhibited by the compounds represented by the formula (I).

Experiment

Five-week-old male rats of the Wister-King strain were fed with solid food (Clea CE-2) for 3 days in groups of 10 rats per cage. From the fourth day, rats were fed with powdered food (Clea CE-2) under conditions of one rat per cage, the cages being made of polyethylene with wood floors.

The body weight and the amount of food easten by each rat were measured every day around 10-11 o'- clock. Rats whose weight increase and food consumption were stable were selected, and, two weeks after the feeding began, were subjected to the test.

The rats were divided into groups of 3 rats each. They were kept in a light environment from 7 a.m. to 7 p.m. and in a dark environment from 7 p.m. to 7 a.m.

The rats in the following groups were treated as follows:

(1) One ml of an aqueous solution of 1-deoxyglucosamine (1.44 g/3 ml) was intraperitoneally administered;

(2) One ml of an aqueous solution of 1-deoxyglucosamine (4.32 g/3 ml) was orally administered;

(3) One ml of an aqueous solution of 1-deoxy-N-acetylglucosamine (2.955 g/6 ml) was orally administered;

(4) Three ml of an aqueous suspension of 1-deoxy-tetraacetylglucosamine (4.77 g/9 ml) was orally administered;

(5) One ml of an aqueous solution of D-glucose (1.29 g/3 ml) was intraperitoneally administered;

(6) One ml of physiological saline was intraperitoneally administered; and (7) Untreated.

The medicine was administered at 6 p.m. on the testing day, and the food consumption and body weight of each rat were measured every day for the next three days.

Figure 2:
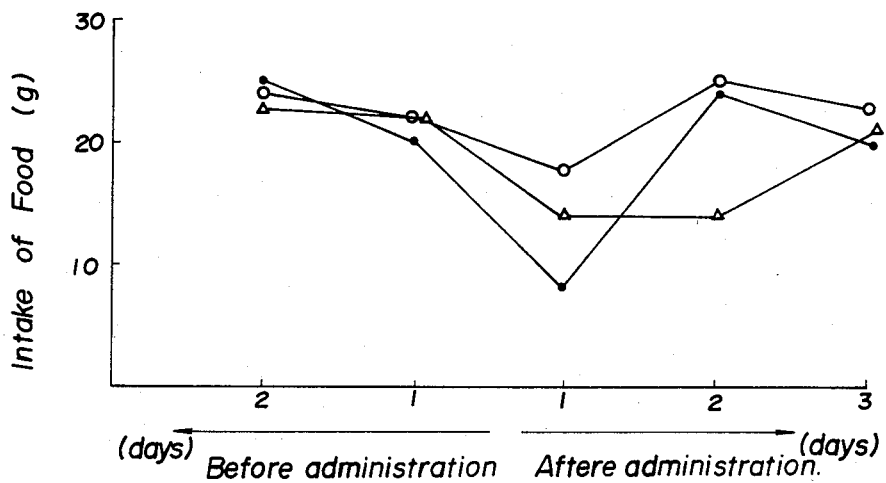
Figure 3:
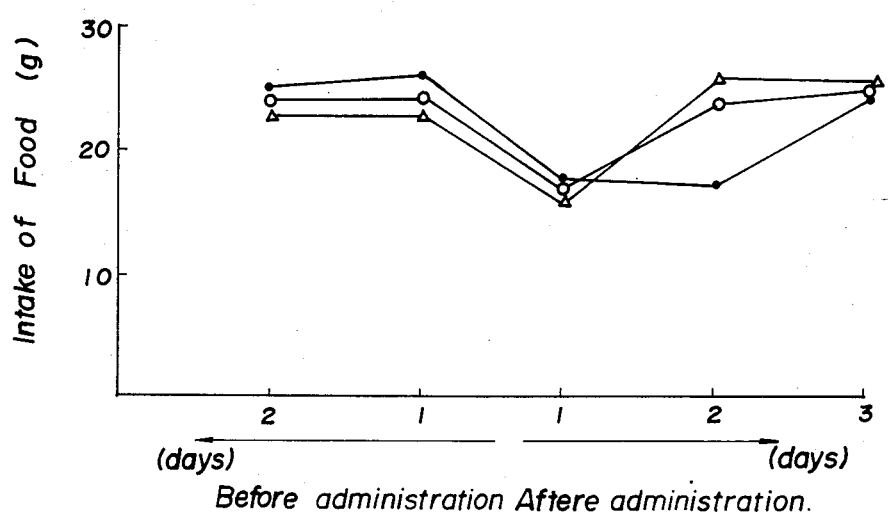
Figure 4:
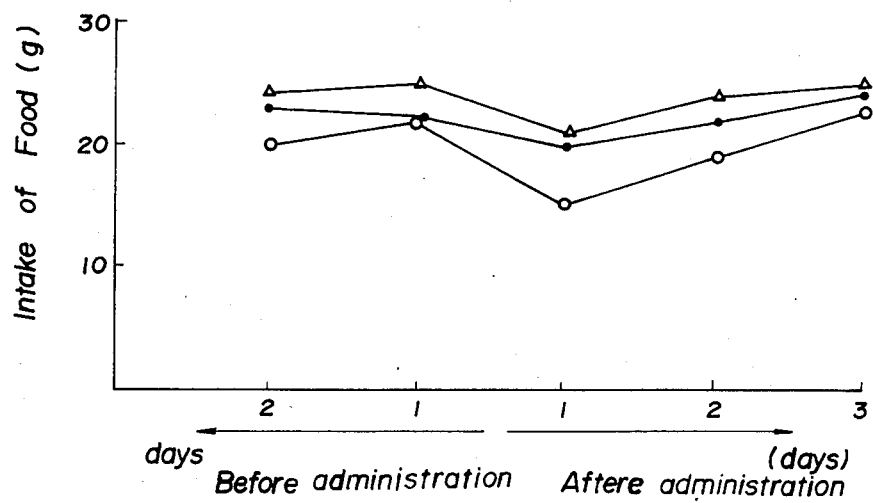
Figure 5:
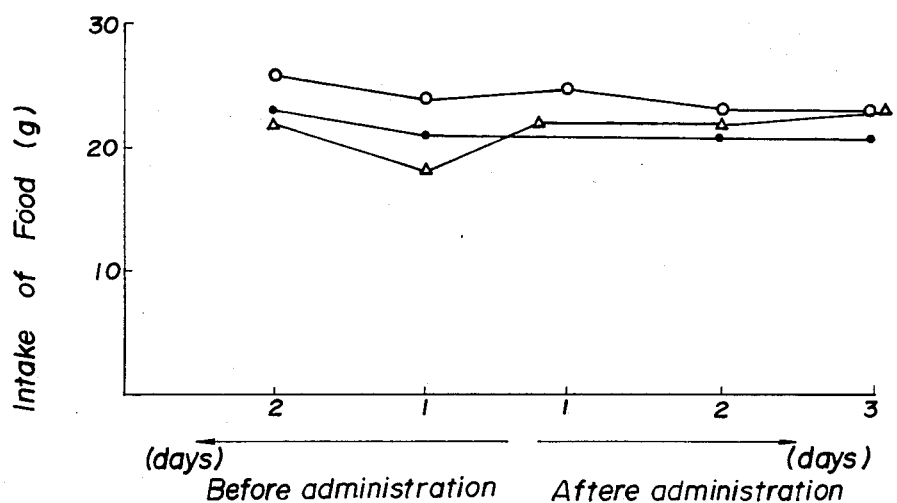
Figure 6:
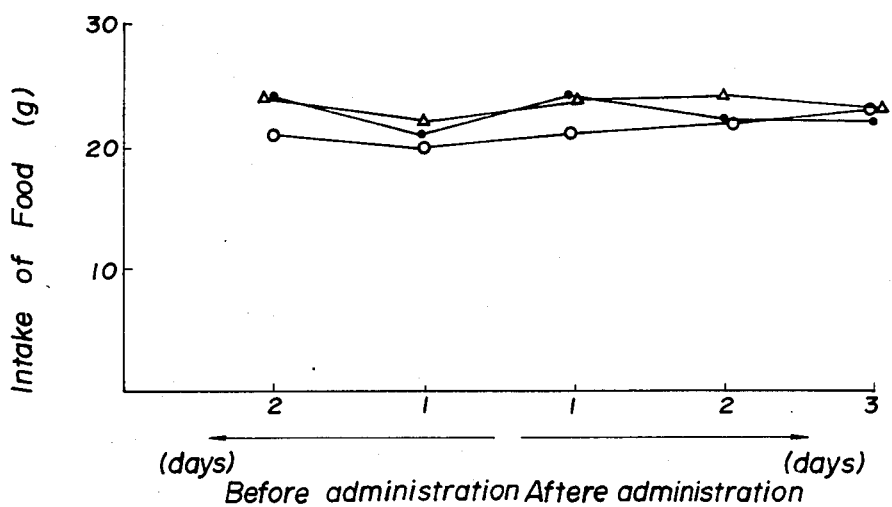
Figure 7:
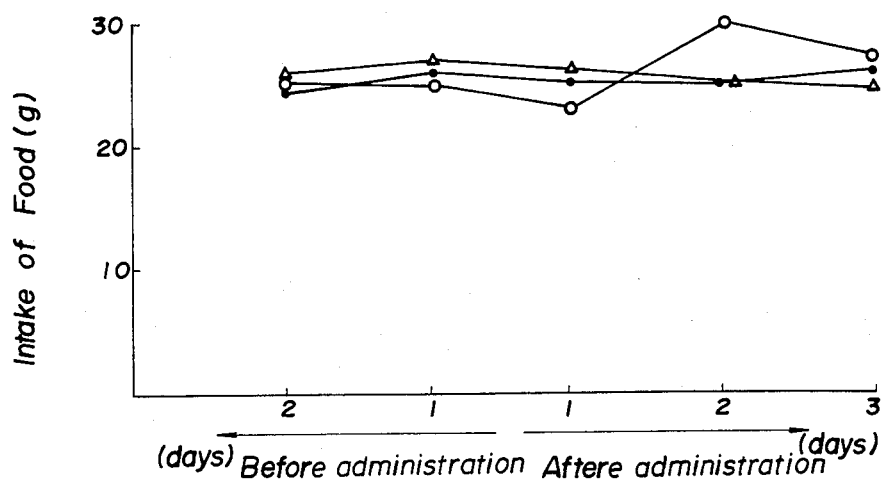
Figure 8:
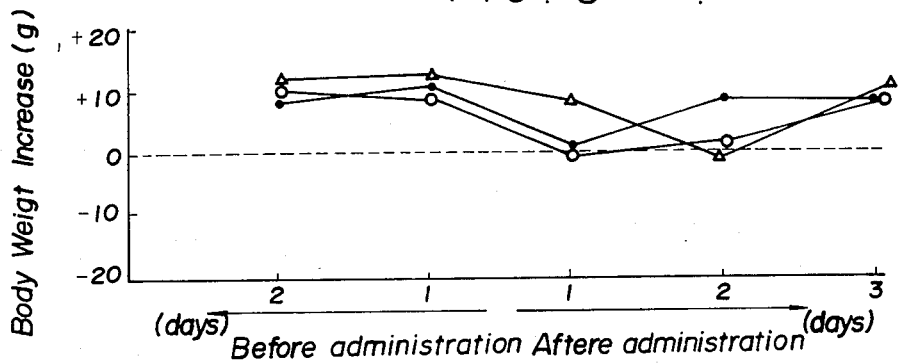
Figure 9:
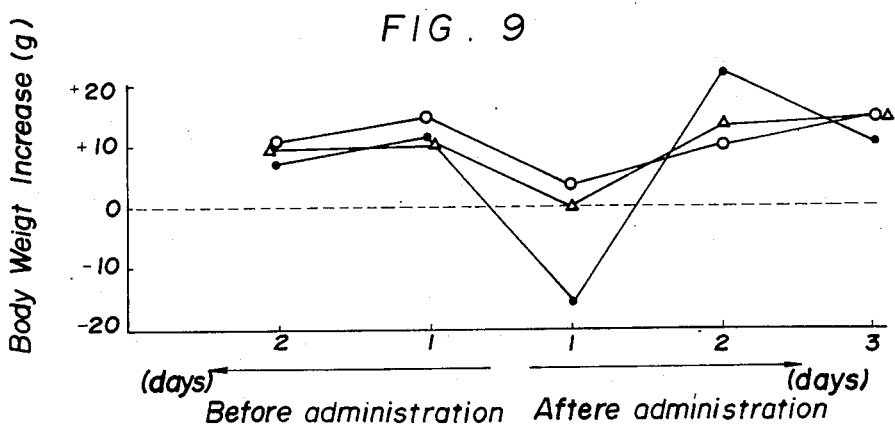
Figure 10:
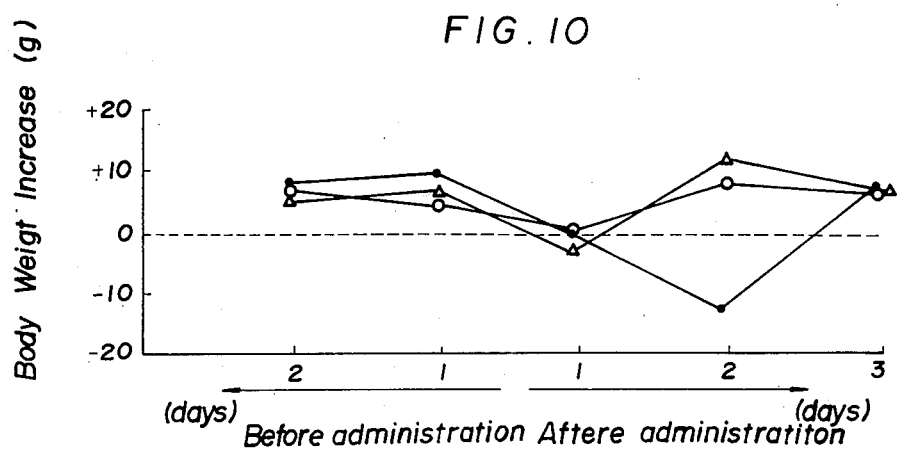
Figure 11:
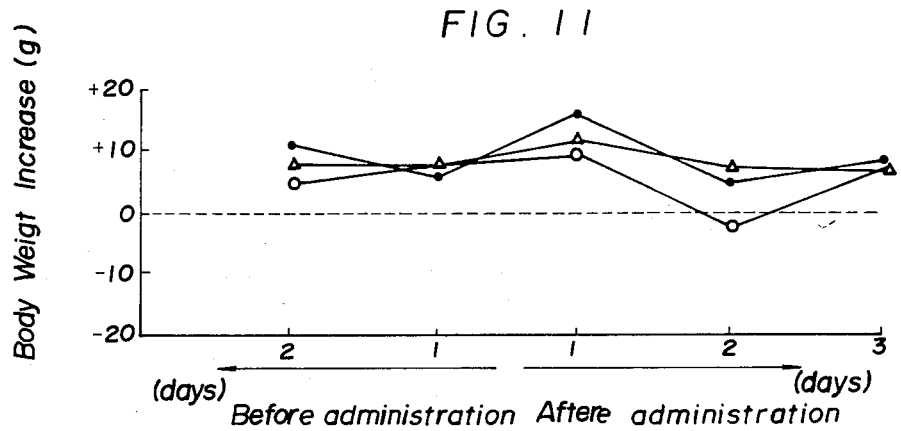
Figure 12:
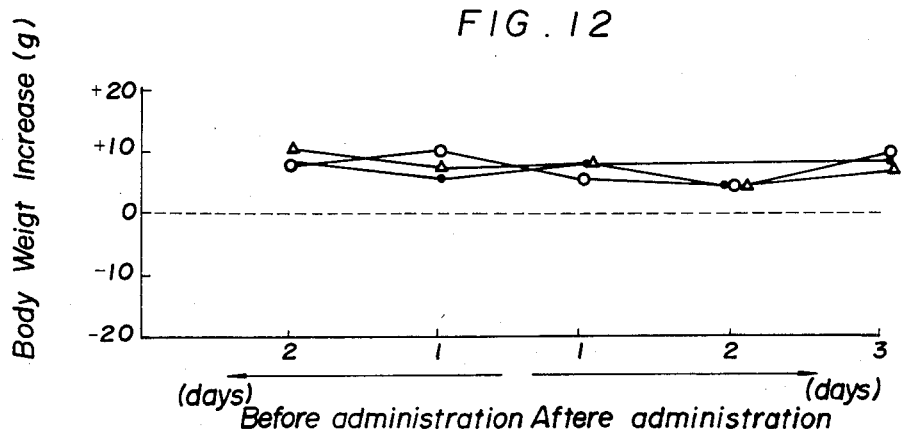

The test results are shown in graphs in FIG. 1 to FIG. 14.

FIGS. 1-7 show food intake patterns of the rats in each group. In the graphs, the vertical axis represents the amount of food taken in terms of grams per day, and the horizontal axis shows day before and after administration of the test compound.

FIGS. 8-14 show profiles of percent weight increase of rates in each group in comparison with the weight of the previous day, the vertical axis representing percent weight increase (g/day), and the horizontal axis showing time passage in terms of days before and after the administration.

As is clear from the graphs in FIGS. 1-14, rats in each of the untreated, glucose-administered, and physiological saline-administered groups showed normal intake of food and weight increase. In contrast, food intake of rats administered with the compound of this invention was depressed over a desired period of time, and the rats showed significant depression of weight increase.

The present invention is further illustrated by the following Examples.

EXAMPLE 1

Preparation of granules or fine granules

| Components | Amount (g) |
|---|---|
| 1-Deoxyglucosamine | 50 |
| Lactose | 9500 |
| Hydroxypropylcellulose | 400 |
| Starch | 50 |

All of the components were mixed thoroughly and formed into granules by the conventional method.

EXAMPLE 2

Preparation of capsules

| Components | Amount (g) |
|---|---|
| 1-Deoxy-N—acetylglucosamine | 100 |
| Starch | 1850 |
| Magnesium stearate | 50 |

All of the components were mixed thoroughly, and gelatin capsule skins were filled with the mixture in an amount corresponding to 10 mg of the active component per capsule to form 10,000 capsules.

EXAMPLE 3

Preparation of tablets

| Component | Amount (g) |
|---|---|
| 1-Deoxy-terraacetylglucosamine | 1000 |
| Lactose | 3500 |
| Starch | 1200 |

All the components were mixed thoroughly, and the mixture was formed into tablets by a conventional method thereby making 100,000 tablets each of which contained 10 mg of the active component.

EXAMPLE 4

Preparation of solution for Injections

1-Deoxyglucosamine hydrochloride (50 g) was dissolved in 10 l of sterilized distilled water to form a sterilized solution for injections.

What is claimed is:

1. A method of preventing or treating obesity by administering to a patient in need of such therapy as the active ingredient, an effective amount of a compound of the formula

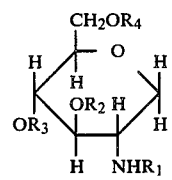

wherein $R_1$, $R_2$, $R_3$ and $R_4$ are the same or different and are selected from a hydrogen atom or an acetyl group or a pharmaceutically acceptable acid addition salt thereof.

2. A method according to claim 1 wherein said active ingredient is 1-deoxyglycosamine or its pharmaceutically acceptable acid addition salt.

3. A method according to claim 2 wherein said acid addition salt is the hydrochloride.

4. A method according to claim 1 wherein said active ingredient is 1-deoxy-N-acetylglucosamine.

5. A method according to claim 1 wherein said active ingredient is 1-deoxy-tetraacetylglucosamine.

6. A method according to claim 1 wherein said active ingredient is administered in an amount of from 50 to 1000 mg/day.

* * * * *